(12) United States Patent
Smith, Jr. et al.

(10) Patent No.: US 7,141,705 B2
(45) Date of Patent: Nov. 28, 2006

(54) ETHERIFICATION PROCESS

(75) Inventors: Lawrence A. Smith, Jr., Houston, TX (US); John R. Adams, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 19 days.

(21) Appl. No.: 10/926,208

(22) Filed: Aug. 25, 2004

(65) Prior Publication Data

US 2006/0030741 A1 Feb. 9, 2006

Related U.S. Application Data

(60) Provisional application No. 60/599,177, filed on Aug. 5, 2004.

(51) Int. Cl.
*C07C 41/06* (2006.01)

(52) U.S. Cl. .................................. 568/697; 568/699

(58) Field of Classification Search ................ 568/697, 568/699
See application file for complete search history.

(56) References Cited

U.S. PATENT DOCUMENTS

| | | | |
|---|---|---|---|
| 2,403,672 A | 7/1946 | Matsuszak | |
| 3,091,586 A | 5/1963 | Pappas et al. | |
| 3,121,124 A | 2/1964 | Verdol | |
| 3,170,000 A | 2/1965 | Verdol | |
| 3,270,081 A | 8/1966 | Verdol | |
| 3,317,593 A | 5/1967 | Enk et al. | |
| 3,531,539 A | 9/1970 | Tidwell | |
| 3,629,478 A | 12/1971 | Haunschild | |
| 3,634,534 A | 1/1972 | Haunschild | |
| 3,726,942 A | 4/1973 | Louder | |
| 3,825,603 A | 7/1974 | Massie | |
| 3,846,088 A | 11/1974 | Brown et al. | |
| 3,940,450 A | 2/1976 | Lee | |
| 4,100,220 A | 7/1978 | Bowman et al. | |
| 4,198,530 A | 4/1980 | Wentzheimer et al. | |
| 4,215,011 A | 7/1980 | Smith, Jr. | |
| 4,232,177 A | 11/1980 | Smith, Jr. | |
| 4,336,407 A | 6/1982 | Smith, Jr. | |
| 4,482,775 A * | 11/1984 | Smith, Jr. ................ | 585/671 |
| 4,504,687 A | 3/1985 | Jones, Jr. | |
| 4,978,807 A | 12/1990 | Smith, Jr. | |
| 5,118,873 A | 6/1992 | Smith, Jr. | |
| 5,190,730 A * | 3/1993 | Smith et al. ............... | 422/109 |
| 5,248,837 A | 9/1993 | Smith, Jr. et al. | |
| 5,313,005 A | 5/1994 | Smith, Jr. et al. | |
| 5,530,165 A * | 6/1996 | Facker et al. ............. | 568/697 |
| 5,569,787 A * | 10/1996 | Rastelli et al. ........... | 568/697 |
| 6,232,509 B1 | 5/2001 | Smith, Jr. et al. | |
| 6,583,325 B1 | 6/2003 | Smith, Jr. et al. | |

OTHER PUBLICATIONS

H. Scheeline and S. Terada, Methyl Tertiary Butyl Ether, Process Economics Reviews, SRI International, Menlo Prk, California.

* cited by examiner

*Primary Examiner*—Rosalynd Keys
(74) *Attorney, Agent, or Firm*—Kenneth H. Johnson

(57) ABSTRACT

A process for the etherification of $C_4$, $C_5$ and/or $C_6$ tertiary olefins in a hydrocarbon feed with at least one $C_1$ to $C_6$ alcohol, preferably $C_1$–$C_4$ alcohols in a distillation column reactor, preferably where $C_4$'s and $C_5$'s ethers are co-produced, in which the amount of alcohol employed in the etherification is below that which will produce an azeotrope with hydrocarbons in the overheads from the distillation column reactor. The azeotrope results from the presence of unreacted alcohol in the reaction system in the distillation column reactor. The amount of alcohol is less than the stoichiometric amount, preferably less than 90%, more preferably 10 to 80%, of the stoichiometric amount and the overheads contain less than a stoichiometric of alcohol.

2 Claims, No Drawings

ETHERIFICATION PROCESS

This application claims the benefit of provisional application 60/599,177 filed Aug. 5, 2004.

BACKGROUND OF THE INVENTION

1. Field of the Invention

The present invention relates to the etherification reaction of $C_4$, $C_5$ and/or $C_6$ isoolefins with lower alcohols, such as methanol, to produce the corresponding tertiary ether. More particularly the invention relates to a process wherein a catalytic distillation process is carried out under conditions to avoid an azeotrope of alcohol with the hydrocarbons.

2. Related Information

Some ethers have been suggested to be detrimental as gasoline additives, because their presence has been detected in ground water. However, the ethers continue to be a valuable source of oxygenates to improve octane levels for reformulated gasoline. The increased governmental restriction on gasoline has strained the availability of feed stocks for etherification. The use of the isoamylenes for the preparation of octane improvers for gasoline has increased as has isohexene. It is highly desirable to be able to employ mixed isobutene/isoamylene and isobutene/isoamylene/isohexene streams.

The reaction of an alcohol and an olefin and concurrent separation of the reactants from the reaction products by fractional distillation has been practiced for some time. The process is variously described in U.S. Pat. Nos. 4,232,177; 4,307,254; 4,336,407; 4,504,687; 4,987,807; and 5,118,873. The isoolefins preferably react with the alcohol to form ethers. Briefly the alcohol and isoolefin are fed to a distillation column reactor having a distillation reaction zone containing a suitable catalyst, such as an acid cation exchange resin, in the form of a catalytic distillation structure, and also having a distillation zone containing an inert distillation structure. Tertiary olefins react preferably to the normal olefins.

U.S. Pat. No. 5,248,837 discloses a method for controlling catalytic distillation etherifications wherein the methanol concentration below the catalyst bed is controlled to a point that maximizes ether production and prevents alcohol from leaving with the bottoms ether product.

U.S. Pat. No. 5,313,005 discloses a similar process to U.S. Pat. No. 5,248,837 wherein the alcohol content is controlled by total oxygen in the form of OH. This system is particularly useful when a mixture of alcohols is used.

In the etherification of olefins with alcohol heretofore it was preferable that an excess of the alcohol be available in the reactor. This means that there is an excess of methanol in the reaction distillation zone of the distillation column reactor. Under these conditions in the distillation column reactor the methanol forms a minimum boiling azeotrope with either of the olefins. In the case where $C_4$ components are present the azeotrope is only slightly more volatile than the $C_4$'s alone, and therefore the methanol tends to remain in a relatively constant concentration with the $C_4$'s throughout the column. The concentration of the methanol in the $C_4$ azeotrope is about 4% (depending upon the composition of the $C_4$ mixture and operating pressure of the column), and it is necessary to operate with a methanol concentration to satisfy this azeotrope before the $C_5$ azeotrope can be satisfied.

In maximized ether production reactions using excess alcohol the $C_5$ azeotrope contains about 12 wt % methanol, and the boiling point of the azeotrope is 10 to 15° F. below that of the corresponding $C_5$'s, but above the $C_4$'s and $C_4$/methanol azeotrope. If the net methanol flow into the column is higher than the azeotrope, the methanol concentration will increase (60% has been measured) until methanol leaves with the TAME bottoms product. Similar considerations apply to the $C_6$ streams.

In addition to the considerations of azeotopes discussed above, when two or more different alcohols are fed at the same time, other factors affect the operation of the etherification. For example, in the case of etherification of $iC_5^=$ with a mixed methanol/ethanol stream to produce TAME and tertiary amyl ethyl ether (TAEE), there are two different azeotropes. The first is methanol with the $C_5$'s which is 12% methanol. The second is the azeotrope between the $C_5$'s and the ethanol which is 8% ethanol. The different alcohols also react at different rates with the isoolefins, e.g., methanol reacts more rapidly than ethanol with isopentenes.

It is an advantage of the present invention that the alcohol/hydrocarbon azeotrope can be reduced or eliminated using the present process. It is a further advantage that the amount of ether in the gasoline mix can be reduced while enhancing the dimer production. The dimers (olefins) can be reduced or eliminated by hydrogenation, e.g., diisobutene hydrogenates to isooctane. Since the alcohol is maintained at the partial stoichiometric amount, it is another advantage that the process is easier to operate on a commercial scale, because the alcohol can be substantially eliminated as a down stream problem.

SUMMARY OF THE INVENTION

The present process is an improvement in the etherification of $C_4$, $C_5$ and/or $C_6$ tertiary olefins in a hydrocarbon feed with at least one $C_1$ to $C_6$, preferably $C_1$–$C_4$ alcohol in the presence of an acid catalyst in a distillation column reactor under conditions of concurrent reaction and distillation, preferably where $C_4$, $C_5$ and/or $C_6$ ethers are co-produced, wherein the improvement is the use of an amount of alcohol that will result in an overheads having a lesser amount of alcohol than the azeotropic amount with hydrocarbons, preferably the amount of alcohol is below that which will produce an azeotrope with hydrocarbons under said conditions of concurrent reaction and distillation. The azeotrope results from the presence of unreacted alcohol in the reaction system in the distillation column reactor. It has been found that even at a stoichiometric amount of alcohol, a portion of the alcohol does not react and an azeotrope of hydrocarbons ($C_4$, $C_5$ and $C_6$) is formed in the overheads, which results in the necessity to treat the overheads to remove alcohol. Thus it is preferable that the amount of alcohol be less than the stoichiometric amount, more preferably less than 90% of the stoichiometric amount, most preferably in the range of 10 to 80%. The term "stoichiometric amount" as used herein shall mean that amount of alcohol calculable to be necessary to react with all of the tertiary olefin in the feed.

A preferred embodiment of the process for the co-production of ethers from the reaction of the isobutene and isoamylenes contained in a mixed $C_4/C_5$ stream comprises the steps of:

(a) feeding less than 90%, preferably in the range of 10 to 80% of the stoichiometric amount of at least one $C_1$–$C_4$ alcohol to react with said isobutene and said isoamylenes and a mixture comprising $C_5$ hydrocarbons including pentanes, n-pentenes and isoamylenes and $C_4$ hydrocarbons including butanes, n-butenes and isobutene to a reaction mixture to a distillation column reactor;

(b) concurrently in said distillation column reactor:
   (i) reacting a portion of the said isobutene and said isoamylenes with alcohol to form methyl tertiary butyl ether and tertiary amyl methyl ether in a reaction mixture containing methyl tertiary butyl ether, tertiary amyl methyl ether and reacting a portion of said isobutene and isoamylenes to form dimers thereof,
   (ii) separating said methyl tertiary butyl ether and said tertiary amyl methyl ether and dimers contained in said reaction mixture from said unreacted $C_4$'s, unreacted $C_5$'s contained in said second reaction mixture by fractional distillation;
(c) removing said unreacted $C_4$'s and $C_5$'s from said distillation column reactor as overheads, containing less than an azeotropic amount of alcohol, preferably the overheads are substantially free of alcohol; and
(d) removing said methyl tertiary butyl ether and said tertiary amyl methyl ether and dimers from said distillation column as bottoms.

The term "substantially free of alcohol" is understood to mean that the alcohol may be present in amount of a few ppm to several thousand ppm, e.g., 50–2000 ppm.

In an alcohol free reaction, oligomerization will occur between the olefins, particularly the more reactive tertiary olefins. Under the conditions of temperature and pressure using acid catalysts the oligomers are a mixture being mainly dimer and trimer. The presence of an oxygenate, such as alcohol and/or ether, enhances the dimerization product. Thus, the present low amounts of process alcohol will reduce or eliminate the need to recover and recycle the alcohol in the overheads and encourage the production of valuable dimer.

As used herein the term "distillation column reactor" means a distillation column which also contains catalyst such that reaction and distillation are going on concurrently in the column. In a preferred embodiment the catalyst is prepared as a distillation structure and serves as both the catalyst and distillation structure.

DESCRIPTION OF THE PREFERRED EMBODIMENTS

U.S. Pat. Nos. 5,003,124 and 4,950,803 disclose a liquid phase process for the etherification and oligomerization of $C_4$ or $C_5$ isoolefins with $C_1$ to $C_6$ alcohols in a boiling point fixed bed reactor which is controlled at a pressure to maintain the reaction mixture at its boiling point and which may be directly attached to a catalytic distillation reactor.

In one embodiment of the present process, the olefin and alcohol are first fed to a fixed bed reactor wherein most of the olefin is reacted to form the corresponding ether, e.g., methyl tertiary butyl ether (MTBE) and tertiary amyl methyl ether (TAME) and dimers and other oligomers. The fixed bed reactor is operated at a given pressure such that the reaction mixture is at the boiling point, thereby removing the exothermic heat of reaction by vaporization of the mixture. The fixed bed reactor and process are described more completely in U.S. Pat. No. 4,950,803 which is hereby incorporated by reference.

The effluent from the fixed bed reactor is then fed to the distillation column reactor wherein the remainder of the $iC_4^=$'s or $iC_5^=$'s (or $iC_6^=$ in some instance) is converted to oligomers, selectively the dimers, most all of the methanol having been reacted in the boiling point prereactor. The $C_4$, $C_5$ or $C_6$ olefin stream generally contains only about 10 to 60% olefin, the remainder being inerts which are removed in the overheads from the distillation column reactor substantially free of alcohol.

The catalytic distillation process employs a catalyst system (See U.S. Pat. Nos. 5,730,843; 4,302,356; and 4,215,011) which provides for both reaction and distillation concurrently in the same reactor, at least in part within the catalyst system. The method involved is briefly described as one where concurrent reaction and distillation occur in combination reaction-distillation structures which are described in several U.S. Patents, namely U.S. Pat. Nos. 4,242,530; 4,250,052; 4,232,177; 4,302,356; 4,307,254; and 4,336,407. Additionally U.S. Pat. Nos. 4,302,356 and 4,443,559 disclose catalyst structures which are useful as distillation structures.

Typical $C_4$ and $C_5$ hydrocarbon feeds contemplated for this process may comprise:

| COMPONENT | MOLE % RANGE | |
|---|---|---|
| | BROAD | PREFERRED |
| $C_5$'s | 15–85 | 40–70 |
| ISOAMYLENE | 5–30 | 15–25 |
| $C_4$'s | 15–85 | 40–60 |
| ISOBUTENE | 5–35 | 10–20 |
| $C_3$ AND LIGHTER | 0–10 | <5% |
| $C_6$ AND HEAVIER | 0–10 | <5% |

Catalysts preferred for the etherification process are acidic ion exchangers, which contain sulfonic acid groups and which have been obtained by polymerization or copolymerization of aromatic vinyl compounds followed by sulfonation.

The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent specification 908,247).

The ion exchange resin is preferably used in a granular size of about 0.25 to 1 mm, although particles from 0.15 mm up to about 1 mm may be employed.

The resin catalyst is loaded into the fixed bed reactor, which may be used as a guard bed for the catalytic distillation reactor, as a fixed bed of the granules. The feed to the reaction is fed to the bed in liquid phase. The bed may be horizontal, vertical or angled. Preferably the bed is vertical with the feed passing downward through the bed and exiting, after reaction, through the lower end of the reactor.

The catalytic distillation structure must be able to function as catalyst and mass transfer medium. The catalyst must be suitably supported and spaced within the column to act as a catalytic distillation structure. A suitable structure for the catalyst is disclosed in U.S. Pat. No. 5,266,546, which is hereby incorporated by reference. Other catalytic distillation structures useful for this purpose are disclosed in U.S. Pat. Nos. 4,731,229; 5,073,236; 5,431,890; and 5,730,843 which are also incorporated by reference. The catalytic distillation structure when loaded into the column constitutes a distillation reaction zone.

If a guard bed is used the amount of alcohol used must be such as to provide the quantities recited above in the catalytic distillation column. Similarly alcohol may be added to the catalytic distillation column so long as the the alcohol/hydrocarbon azeotope is not formed.

The invention claimed is:

1. A process for the co-production of ethers from the reaction of the isobutene and isoamylenes contained in a mixed $C_4/C_5$ stream comprising the steps of:
   (a) feeding less than 90% of the stoichiometric amount of at least one $C_1$–$C_2$ alcohol to react with said isobutene and isoamylenes in a mixture comprising $C_5$ hydrocarbons including pentanes, n-pentenes and isoamylenes and $C_4$ hydrocarbons including butanes, n-butenes and isobutene to a reaction mixture to a distillation column reactor, characterized in that the amount of alcohol is less than an azeotrope amount;
   (b) concurrently in said distillation column reactor
      (i) reacting a portion of the said isobutene and said isoamylenes with alcohol to form methyl tertiary butyl ether and tertiary amyl methyl ether in a reaction mixture containing methyl tertiary butyl ether, tertiary amyl methyl ether and reacting a portion of said isobutene and isoamylenes to form dimers thereof and
      (ii) separating said methyl tertiary butyl ether and said tertiary amyl methyl ether and dimers contained in said reaction mixture from said unreacted $C_4$'s, unreacted $C_5$'s contained in said second reaction mixture by fractional distillation;
   (c) removing said unreacted $C_4$'s and $C_5$'s from said distillation column reactor as overheads wherein said overheads are substantially free of alcohol; and
   (d) removing said methyl tertiary butyl ether and said tertiary amyl methyl ether and dimers from said distillation column as bottoms.

2. The process according to claim 1 wherein said $C_4$'s comprise 40–60 mole % of the feed and said isobutene comprises 10–20 mole % of said feed and $C_5$'s comprise 40–70 mole % and said isoamylene comprises 15–25 mole % of said feed.

* * * * *